United States Patent
Langan et al.

(10) Patent No.: US 7,826,587 B1
(45) Date of Patent: Nov. 2, 2010

(54) SYSTEM AND METHOD OF FAST KVP SWITCHING FOR DUAL ENERGY CT

(75) Inventors: David Allen Langan, Clifton Park, NY (US); John Eric Tkaczyk, Delanson, NY (US); James Walter LeBlanc, Niskayuna, NY (US); Colin R. Wilson, Niskayuna, NY (US); Xiaoye Wu, Rexford, NY (US); Dan Xu, Schenectady, NY (US); Thomas Matthew Benson, Clifton Park, NY (US); Jed Douglas Pack, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/558,248

(22) Filed: Sep. 11, 2009

(51) Int. Cl.
*H05G 1/60* (2006.01)
(52) U.S. Cl. ............................. 378/16; 378/20
(58) Field of Classification Search ............... 378/4–19, 378/98.8, 98.9
See application file for complete search history.

(56) References Cited

U.S. PATENT DOCUMENTS

| | | | |
|---|---|---|---|
| 3,946,261 A | 3/1976 | Holland et al. | |
| 4,109,151 A | 8/1978 | Pieil | |
| 4,541,106 A | 9/1985 | Belanger et al. | |
| 4,799,248 A | 1/1989 | Furbee et al. | |
| 6,052,433 A | 4/2000 | Chao | |
| 6,683,934 B1 | 1/2004 | Zhao et al. | |
| 2006/0109951 A1 | 5/2006 | Popescu | |
| 2007/0041490 A1 | 2/2007 | Jha et al. | |
| 2007/0102642 A1* | 5/2007 | Spahn | 250/363.04 |
| 2007/0140428 A1 | 6/2007 | Toth | |
| 2008/0123812 A1 | 5/2008 | Sabol et al. | |
| 2010/0104062 A1 | 4/2010 | Wu et al. | |

OTHER PUBLICATIONS

Kalender et al., "Evaluation of a prototype dual-energy computed tomographic apparatus," Medical Physics, vol. 13, No. 3, May/Jun. 1986, pp. 334-339.

Wu et al., "Monochromatic CT Image Representation via Fast Switching Dual kVp," Medical Imaging 2009: Physics of Medical Imaging, edited by Ehsan Samei, Jiang Hsieh, Proc. of SPIE, vol. 7258, paper [7258-152], Lake Buena Vista, FL, Feb. 8-12, 2009.

(Continued)

*Primary Examiner*—Irakli Kiknadze
(74) *Attorney, Agent, or Firm*—Scott J. Asmus

(57) ABSTRACT

A CT system includes a gantry, an x-ray source, a generator configured to energize the x-ray source to a first kVp and to a second kVp, a detector, and a controller. The controller is configured energize the x-ray source to the first kVp for a first time period, subsequently energize the x-ray source to the second kVp for a second time period, integrate data for a first integration period that includes a portion of a steady-state period of the x-ray source at the first kVp, integrate data for a second integration period that includes a portion of a steady-state period of the x-ray source at the second kVp, compare a signal-to-noise ratio (SNR) during the first integration period ($SNR_H$) and the second integration period ($SNR_L$), adjust an operating parameter of the CT system to optimize an $SNR_H$ with $SNR_L$, and generate an image using the integrated data.

25 Claims, 6 Drawing Sheets

OTHER PUBLICATIONS

Xu et al., "Dual Energy CT via Fast kVp Switching Spectrum Estimation", Medical Imaging 2009: Physics of Medical Imaging, edited by Ehsan Samei, Jiang Hsieh, Proc. of SPIE, vol. 7258, paper [7258-140], Lake Buena Vista, FL, Feb. 8-12, 2009.

Tkaczyk et al., "Quantization of Liver Tissue in Dual kVp Computed Tomography using Linear Discriminant Analysis", Medical Imaging 2009: Physics of Medical Imaging, edited by Ehsan Samei, Jiang Hsieh, Proc. of SPIE vol. 7258, paper [7258-15], Lake Buena Vista, FL, Feb. 8-12, 2009.

Pack et al., "Fast kVp Switching CT Imaging of a Dynamic Cardiac Phantom", Medical Imaging 2009: Physics of Medical Imaging, edited by Ehsan Samei, Jiang Hsieh, Proc. of SPIE vol. 7258, paper [7258-150], Lake Buena Vista, FL, Feb. 8-12, 2009.

Technical Program, SPIE Medical Imaging Conference, Lake Buena Vista, FL, Feb. 8-12, 2009.

Tkaczyk et al., "Quantization of Liver Tissue in Fast-Switched Dual kVp Computed Tomography using Linear Discriminant Analysis", SPIE Medical Imaging Conference, Lake Buena Vista, FL, Feb. 8-12, 2009.

Office Action dated Feb. 11, 2009 on U.S. Appl. No. 12/114,108, filed May 2, 2008, titled Method for Rapid Switching in a Dual-Energy Computed Tomography (CT) System.

* cited by examiner

SYSTEM AND METHOD OF FAST KVP SWITCHING FOR DUAL ENERGY CT

BACKGROUND OF THE INVENTION

The present invention relates generally to diagnostic imaging and, more particularly, to an apparatus and method of acquiring imaging data at more than one energy range using a multi-energy imaging source.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy sensitive (ES), multi-energy (ME), and/or dual-energy (DE) CT imaging system that may be referred to as an ESCT, MECT, and/or DECT imaging system, in order to acquire data for material decomposition or effective Z or monochromatic image estimation. ESCT/MECT/DECT provides energy discrimination. For example, in the absence of object scatter, the system derives the material attenuation at a different energy based on the signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. These two processes are sensitive to the photon energy and hence each of the atomic elements has a unique energy sensitive attenuation signature. Therefore, the detected signals from two energy regions provide sufficient information to resolve the energy dependence of the material being imaged. Furthermore, detected signals from the two energy regions provide sufficient information to determine the materials attenuation coefficients in terms of Compton scatter and photoelectric effect. Alternatively, the material attenuation may be expressed as the relative composition of an object composed of two hypothetical materials, or the density and effective atomic number with the scanned object. As understood in the art, using a mathematical change of basis, energy sensitive attenuation can be expressed in terms of two base materials, densities, effective Z number, or as two monochromatic representations having different keV.

Such systems may use a direct conversion detector material in lieu of a scintillator. The ESCT, MECT, and/or DECT imaging system in an example is configured to be responsive to different x-ray spectra. Energy sensitive detectors may be used such that each x-ray photon reaching the detector is recorded with its photon energy. One technique to acquire projection data for material decomposition includes using energy sensitive detectors, such as a CZT or other direct conversion material having electronically pixelated structures or anodes attached thereto. However, such systems typically include additional cost and complexity of operation in order separate and distinguish energy content of each received x-ray photon.

In an alternative, a conventional scintillator-based third-generation CT system may be used to provide energy separation measurements. Such systems may acquire projections sequentially at different peak kilovoltage (kVp) operating levels of the x-ray tube, which changes the peak and spectrum of energy of the incident photons comprising the emitted x-ray beams. A principle objective of scanning with two distinctive energy spectra is to obtain diagnostic CT images that enhance information (contrast separation, material specificity, etc.) within the image by utilizing two scans at different polychromatic energy states.

A number of techniques have been proposed to achieve energy sensitive scanning including acquiring two scans at, for instance, 80 kVp and 140 kVp (1) back-to-back sequentially in time where the scans require two rotations of the gantry around the subject that may be hundreds of milliseconds to seconds apart, (2) interleaved as a function of the rotation angle requiring one rotation around the subject, or (3) using a two tube/two detector system with the tubes/detectors mounted ~90 degrees apart, as examples. However, taking separate scans several seconds apart from one another may result in mis-registration between datasets caused by patient motion (both external patient motion and internal organ motion) and different cone angles, and cannot be applied reliably where small details need to be resolved for body features that are in motion. A ~90 degree separation in a two tube/two detector system inherently includes a mis-registration of datasets and adds cost and complexity to the overall system.

High frequency, low capacitance generators have made it possible to switch the kVp potential of the high frequency electromagnetic energy projection source on alternating views and interleave datasets. As a result, data for two energy sensitive scans may be obtained in a temporally interleaved fashion rather than with separate scans made several seconds apart or with a two tube/two detector system. However, such systems typically include a change to filament current to account for a changing mAs when kVp potential is switched. The change in filament current can cause a change in filament temperature which, in turn, can cause a change in focal spot position and/or size. Tube voltage may be used in establishing focal spot width with kVp switching, resulting in an oscillating focal spot width. Such changes can cause low and high projections to be misaligned for material decomposition, causing image artifacts that may be manifested particularly at object edges and boundaries. The problem is exacerbated by a relatively long thermal time constant of the tube filament when compared to the desired rate of fast kVp switching.

The change in focal spot position may be addressed through re-sampling of imaging data to mitigate the alignment issue. Or, if there is a significant change in focal spot size, a sinogram having the smaller focal spot may be blurred for improved registration between high and low kVp sinograms. However, these mitigation strategies tend to degrade resolution of the final image.

Alternatively, an x-ray source may be constructed having a pair of cathodes therein, each configured to emit electrons toward an anode, and each having a respective filament current associated therewith. Such a system may accomplish fast kVp switching by, for instance, gridding the cathodes for the respective low and high kVp shots, with each cathode having a low and high kVp applied thereto relative to the anode. Though such a system may avoid the necessity of rapidly altering kVp or mA in a single cathode, it is at the expense of system complexity—both of hardware and system operation.

Therefore, it would be desirable to design a low cost and low complexity apparatus and method of fast switching between energy levels and acquiring imaging data at more than one energy range.

BRIEF DESCRIPTION OF THE INVENTION

Embodiments of the invention are directed to a method and apparatus for acquiring imaging data at more than one energy range that overcome the aforementioned drawbacks.

According to an aspect of the invention, a CT system includes a rotatable gantry having an opening for receiving an object to be scanned, an x-ray source coupled to the gantry and configured to project x-rays through the opening, a generator configured to energize the x-ray source to a first kVp and to a second kVp that is lower than the first kVp, a detector attached to the gantry and positioned to receive x-rays from the x-ray source that pass through the opening, and a controller configured to energize the x-ray source to the first kVp for a first time period subsequently energize the x-ray source to the second kVp for a second time period different from the first, integrate data from the detector for a first integration period that includes a portion of a steady-state period of the x-ray source at the first kVp, integrate data from the detector for a second integration period that includes a portion of a steady-state period of the x-ray source at the second kVp, compare a signal-to-noise ratio (SNR) during the first integration period ($SNR_H$) and the second integration period ($SNR_L$), adjust an operating parameter of the CT system to optimize an $SNR_H$ with $SNR_L$, and generate an image using the integrated data.

According to another aspect of the invention, a method of acquiring energy sensitive CT imaging data using a CT imaging system includes applying a first voltage potential to an x-ray source for a first time duration, applying a second voltage potential to the x-ray source for a second time duration that is greater than the first time duration, acquiring imaging data during a first integration period that includes when the x-ray source emits x-rays at a steady-state at the first potential, acquiring imaging data during a second integration period that includes when the x-ray source emits x-rays at a steady-state at the second potential, optimizing a first signal-to-noise ratio (SNR) during the first integration period with a second SNR during the second integration period by adjusting at least one operating parameter of the CT imaging system, and generating a dual-energy CT image using imaging data acquired after adjusting the at least one operating parameter of the CT imaging system.

According to yet another aspect of the invention, a computer readable storage medium having stored thereon a computer program comprising instructions which when executed by a computer cause the computer to apply a first kVp potential to an x-ray source to obtain a first kVp steady-state operation of a CT imaging system, apply a second kVp potential to the x-ray source to obtain a second kVp steady-state operation of the CT imaging system, integrate a first set of imaging data that includes data obtained from x-rays generated during a time period when the x-ray source is at the first kVp steady-state operation, integrate a second set of imaging data that includes data obtained from x-rays generated during a time period when the x-ray source is at the second kVp stead-state operation, compare a first signal-to-noise ratio (SNR) of the integrated first set of imaging data with a second SNR of the integrated second set of imaging data, and adjust at least one operating parameter of the CT imaging system based on the comparison.

According to still another aspect of the invention, a method of establishing first and second integration periods for acquisition of fast-switching dual-energy CT data in a CT system includes determining a first signal-to-noise ratio (SNR) for the first integration period, determining a second SNR for the second integration period, comparing the first SNR to the second SNR, and adjusting an operating condition of the CT system based on the compared first SNR and the second SNR.

These and other advantages and features will be more readily understood from the following detailed description of preferred embodiments of the invention that is provided in connection with the accompanying drawings.

DETAILED DESCRIPTION OF THE PREFERRED EMBODIMENT

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations, and with systems having a capability of shifting, or "wobbling" the focal spot during operation. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

A dual energy CT system and method is disclosed. Embodiments of the invention support the acquisition of both anatomical detail as well as tissue characterization information for medical CT, and for components within luggage. Energy discriminatory information or data may be used to reduce the effects of beam hardening and the like. The system supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

Figure 1:
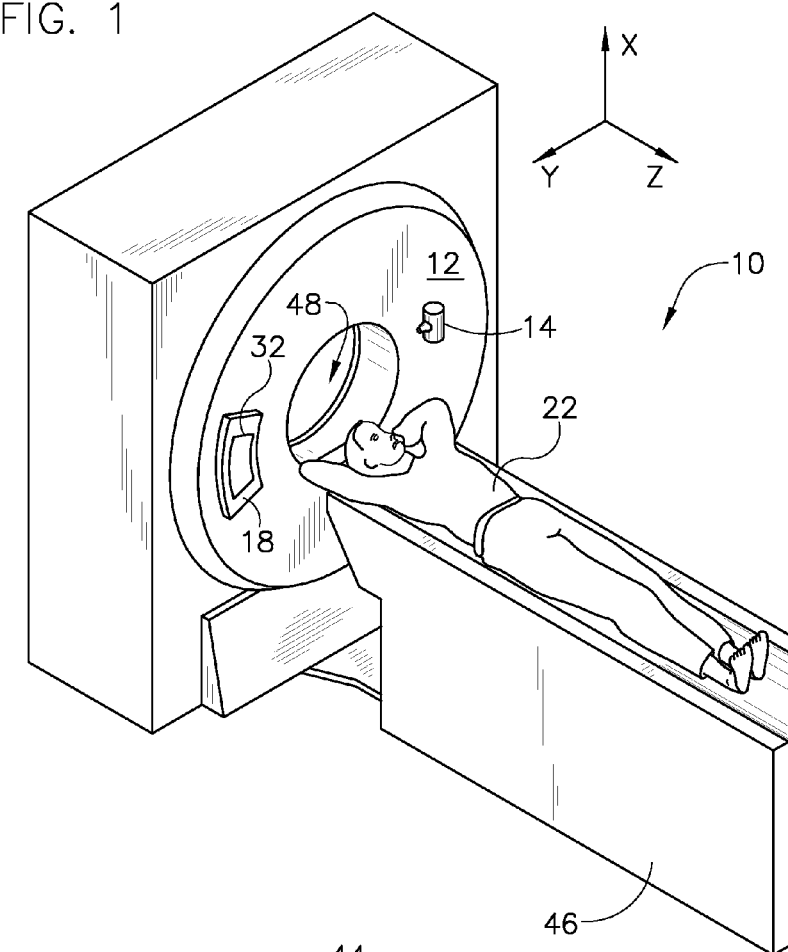
FIG. 1 is a pictorial view of a CT imaging system.
Figure 2:
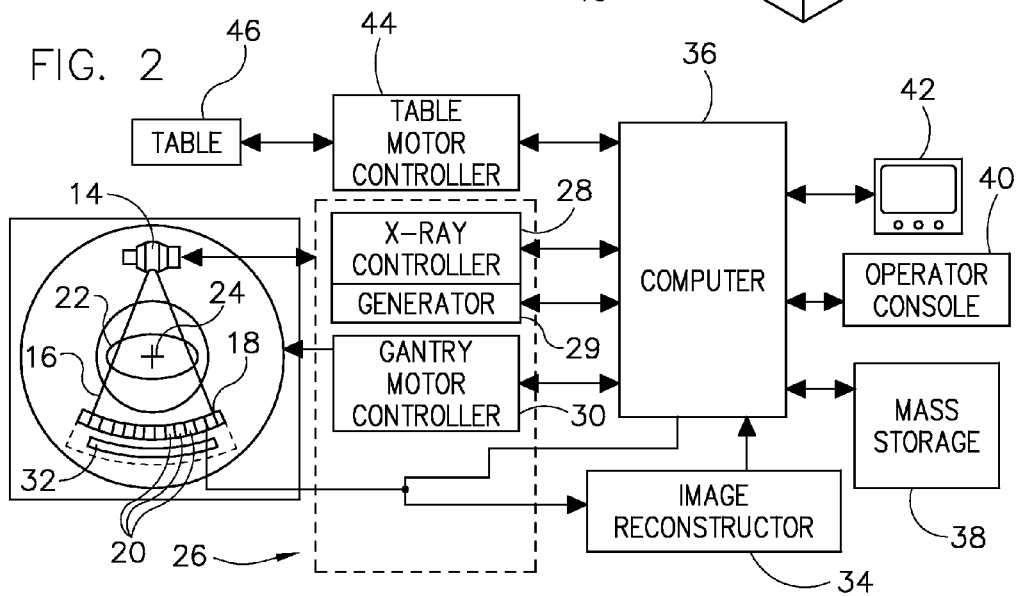
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 that includes a collimator on the opposite side of the gantry 12. In embodiments of the invention, x-ray source 14 includes either a stationary target or a rotating target. Detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 and generator 29 that provides power and timing signals to x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

System 10 may be operated in either monopolar or bipolar modes. In monopolar operation, either the anode is grounded and a negative potential is applied to the cathode, or the cathode is grounded and a positive potential is applied to the anode. Conversely, in bipolar operation, an applied potential is split between the anode and the cathode. In either case, monopolar or bipolar, a potential is applied between the anode and cathode, and electrons emitting from the cathode are caused to accelerate, via the potential, toward the anode. When, for instance, a −140 kV voltage differential is maintained between the cathode and the anode and the tube is a bipolar design, the cathode may be maintained at, for instance, −70 kV, and the anode may be maintained at +70 kV. In contrast, for a monopolar design having likewise a −140 kV standoff between the cathode and the anode, the cathode accordingly is maintained at this higher potential of −140 kV while the anode is grounded and thus maintained at approximately 0 kV. Accordingly, the anode is operated having a net 140 kV difference with the cathode within the tube.

Figure 3:
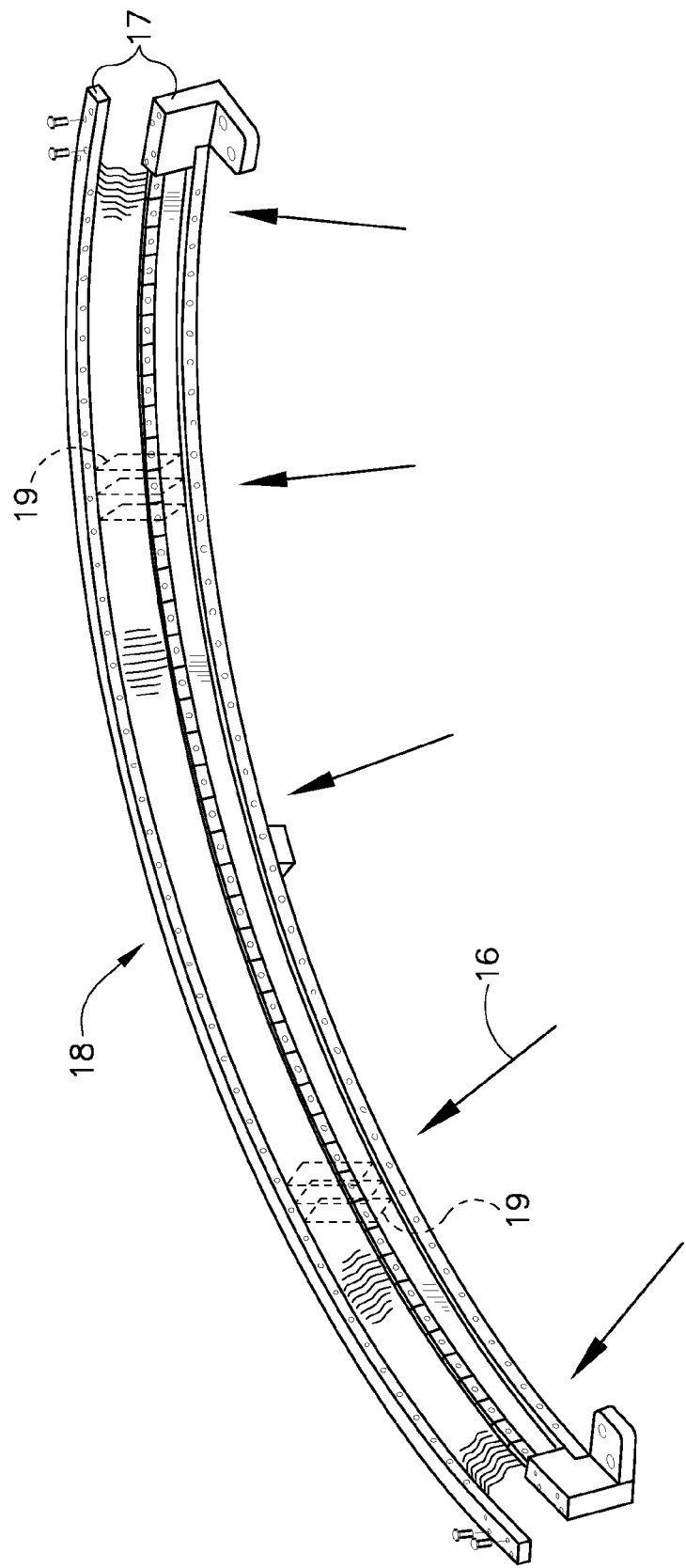
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, such as will be illustrated, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
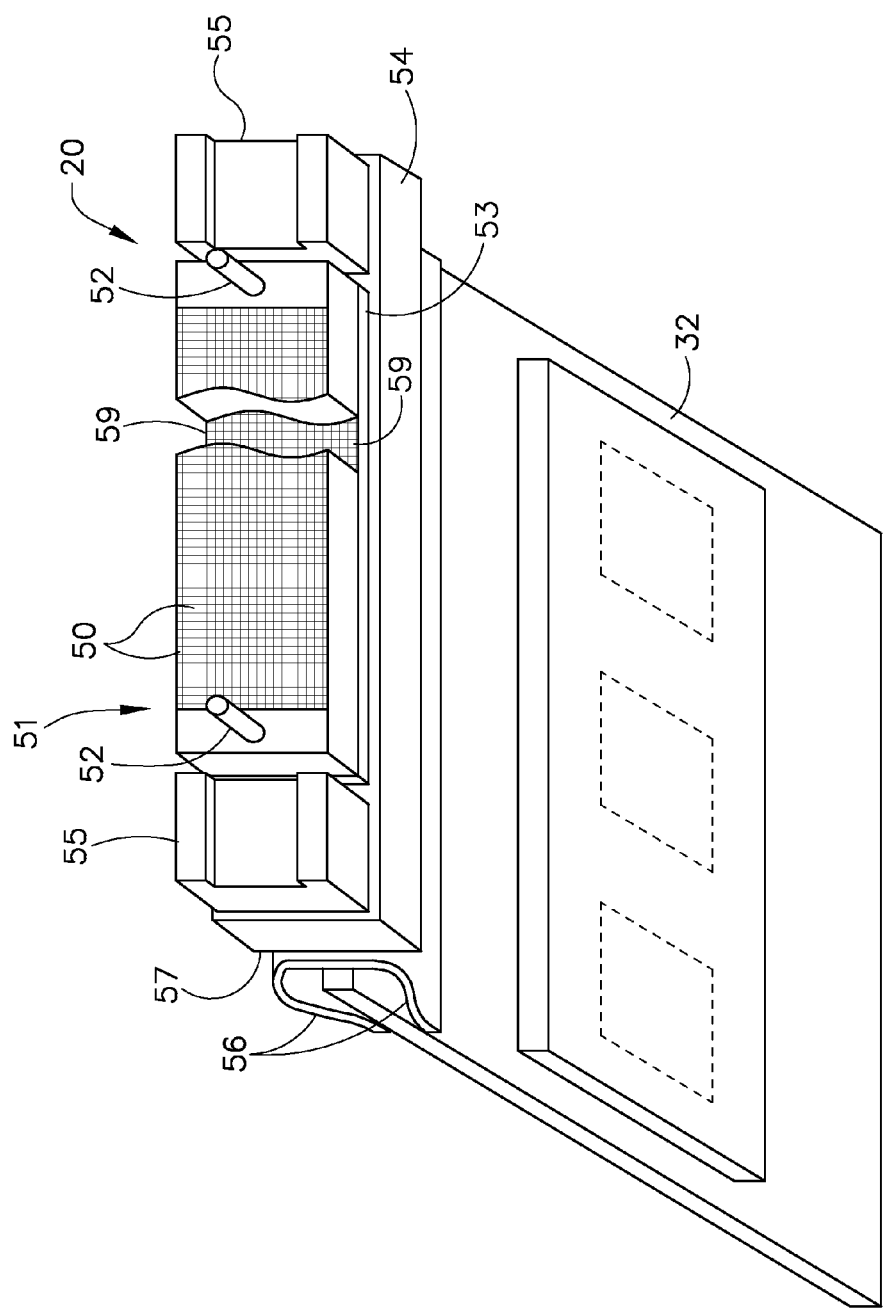
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 5:
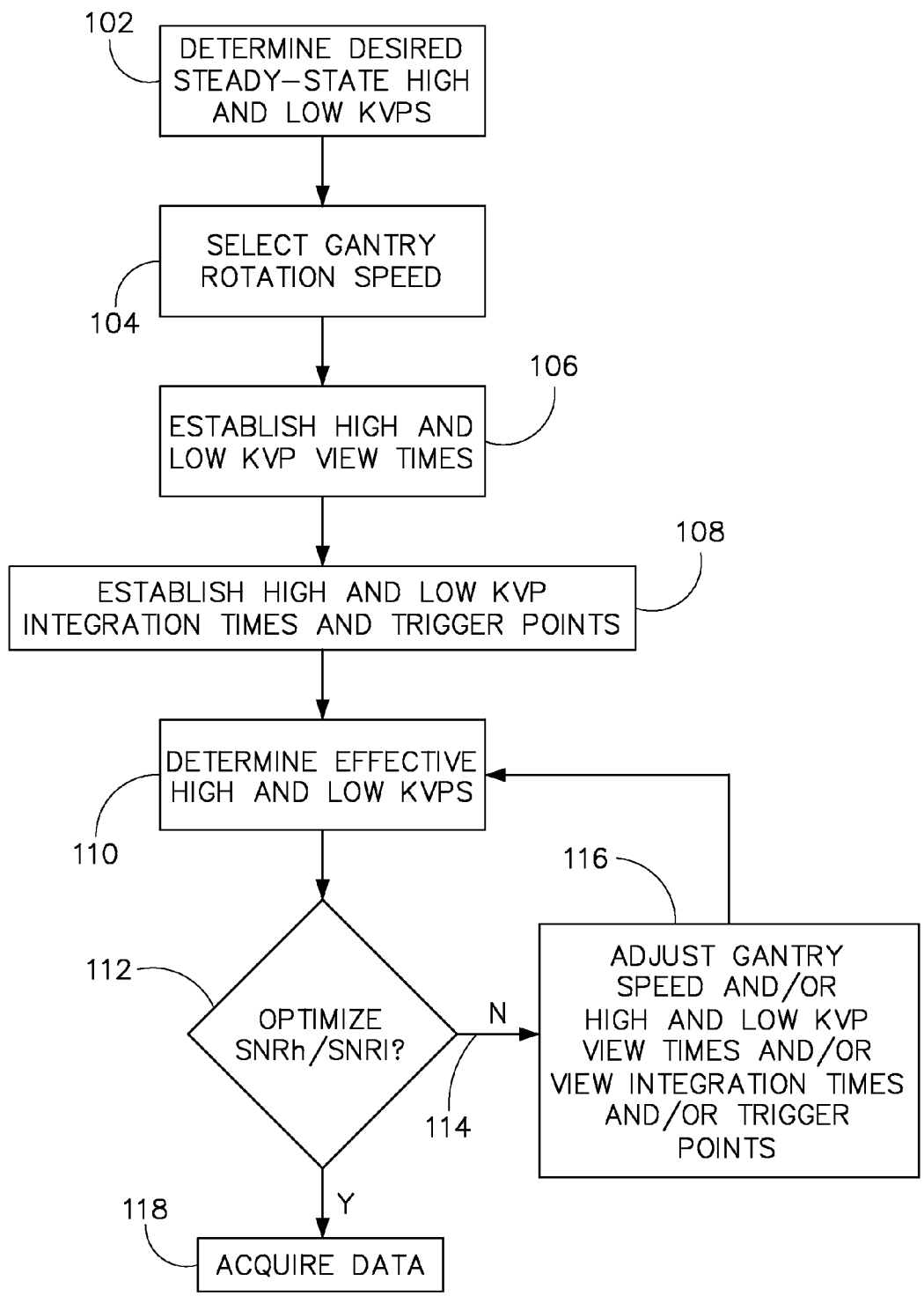
FIG. 5 is a flowchart illustrating acquisition of high and low kVp data sets, according to an embodiment of the invention.

FIG. 5 is a flowchart that illustrates a process 100 for obtaining optimized settings for a CT system to obtain fast kVp switching data, according to an embodiment of the invention. At step 102 desired steady-state high and low kVp settings are established based on a number of criteria. The selection criteria are based on factors that include but are not limited to the object to be imaged, desired energy separation between high and low kVp, system capabilities, system rise and falltimes, and effective low and high kVps. As will be further discussed, effective high and low kVp are to be distinguished from target and steady-state high kVp and low kVp. In one example the desired steady-state high kVp is 140 kVp, and the desired low kVp is 80 kVp, though one skilled in the art will recognize that other desired high and low kVps may be applied, depending on other factors as discussed. For instance, in an application where increased object penetration may be desired or necessary, the low kVp may, in that instance, be increased—but it may be at the expense of energy sensitivity or decreased energy separation between low and high kVp if the high kVp is not, likewise, increased.

At step 104 an application is selected. For a given application, patient motion is inferred thereby specifying a minimum gantry rotation speed in order to "freeze" patient motion, as is understood with the art. As examples, a neuroimaging scan is typically 1 second/revolution gantry speed, an abdominal scan is typically 0.5 second/revolution, and a cardiac scan is typically at 0.35 second/revolution. Further, one skilled in the art will recognize that these times are but examples, and that gantry rotation speeds may be selected based on any imaging application, based on system runspeed capabilities, patient size, and the like. And, as is typically understood in the art and as will be further discussed, ~1000 pairs of high and low kVp acquisitions taken per gantry revolution to achieve sufficient angular sampling necessary for the desired image resolution. This results in sub-millisecond (ms) view acquisitions.

At step 106 high and low kVp view times are established. The view times established are based on a number of factors that include but are not limited to the gantry rotation speed as selected at step 104 and desired angular sampling rates (which is dependent on geometry of gantry 12, geometry of detector assembly 18, and the like). High and low kVp view times are established with a constraint that their sum is a total view time that is established by gantry speed and system geometry. In other words, gantry speed and system geometry establish a total view time, and each total view time includes a high and a low kVp viewtime, according to an embodiment of the invention. As such, once total view time is established, one of the parameters that may be adjusted or iterated upon, according to the invention, is each individual high and low kVp viewtime, but given the constraint that their sum comprises the total viewtime. After establishment of high and low kVp view times at step 106, high and low integration times and trigger points are established at step 108. High and low kVp viewtimes, integration times, and integration trigger points will be discussed and illustrated with respect to FIG. 6.

Figure 6:
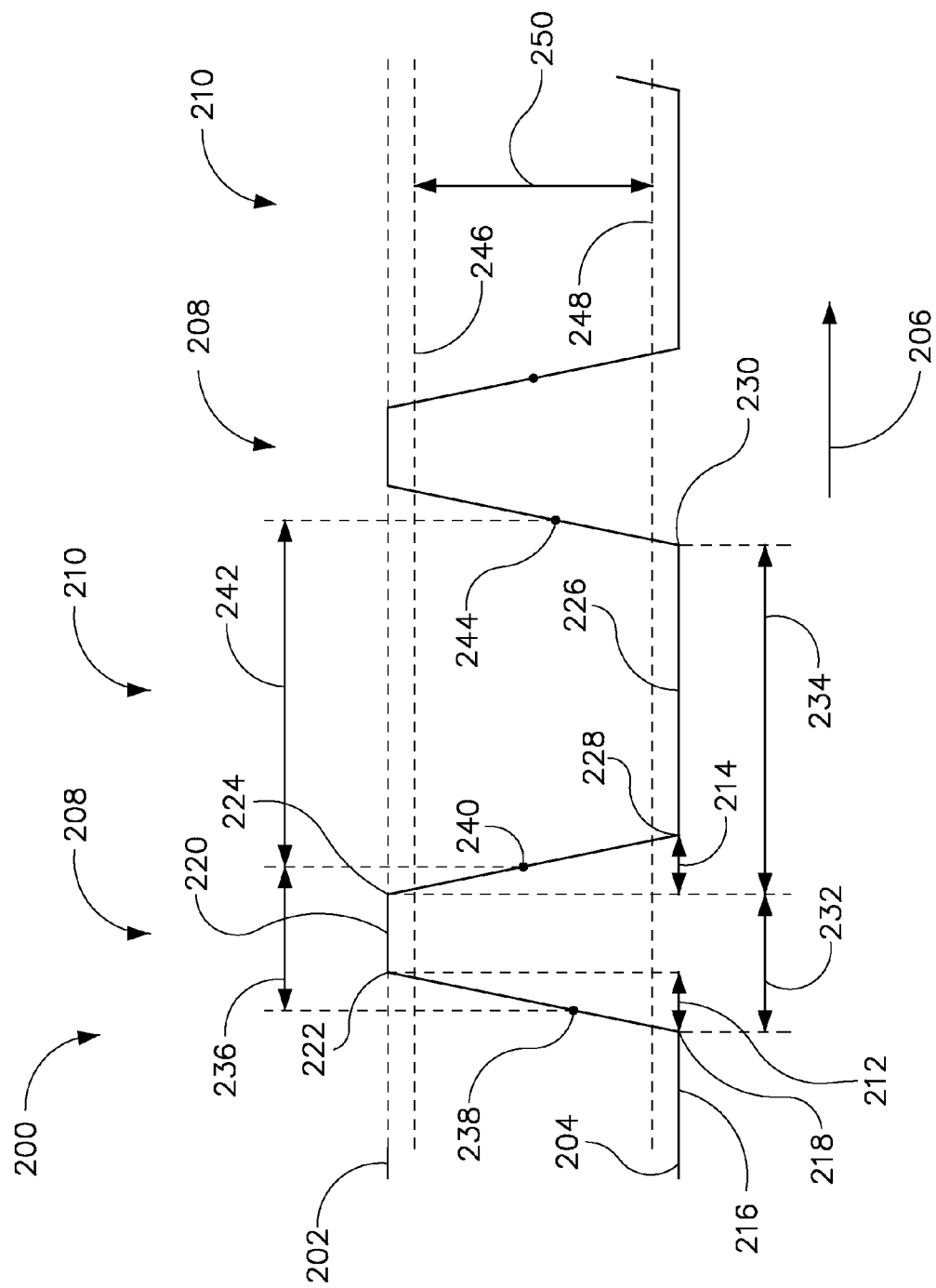
FIG. 6 is a timing diagram illustrating high and low kVp data acquisition, according to an embodiment of the invention.
Figure 7:
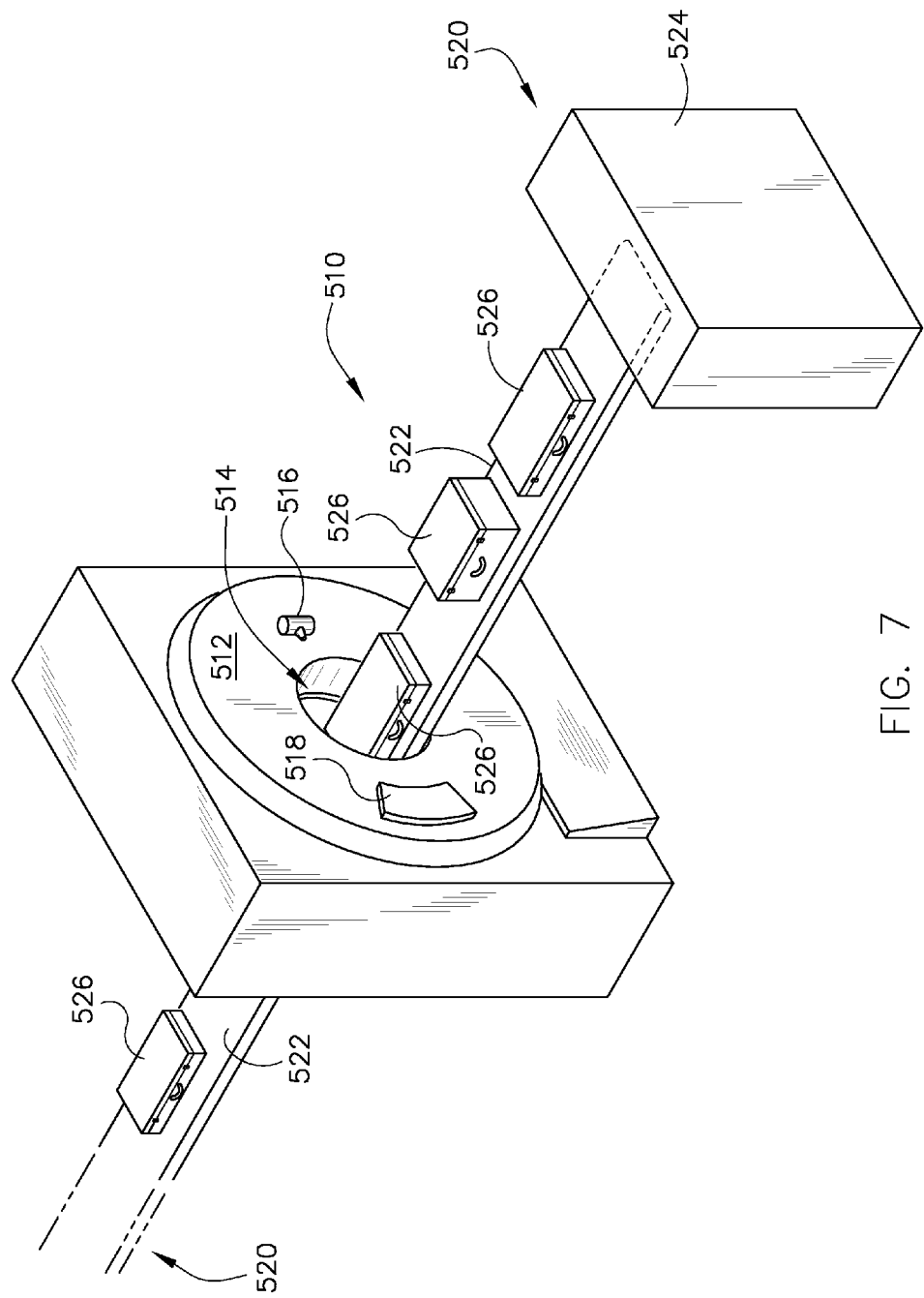
FIG. 7 is a pictorial view of a CT system for use with a non-invasive package inspection system according to an embodiment of the invention.

Referring now to FIG. 6, timing diagram 200 illustrates a repeating pattern of high and low kVp operation according to an embodiment of the invention. Timing diagram 200 includes a desired or target high kVp 202 and a desired or target low kVp 204 against a time axis 206. Timing diagram 200 illustrates high kVp shots 208 and low kVp shots 210, two of which are illustrated, in a repeating pattern. As is understood in the art, switching between high kVp shots 208 and low kVp shots 210 is not instantaneous, thus each transition from low kVp to high kVp includes a respective risetime 212 and a falltime 214. Risetime 212 and falltime 214 are on the order of 100 μs in one embodiment, but may be faster or slower than 100 μs depending on system hardware capacitance and other factors as understood within the art.

In operation, low kVp is illustrated beginning at steady-state at 216. At point 218, target high kVp 202 is applied and a steady-state high kVp 220 is achieved, beginning at point 222 after risetime 212. At point 224, target low kVp 204 is applied and a steady-state low kVp 226 is achieved, beginning at point 228 after falltime 214. Target high kVp 202 is again applied at point 230, and the pattern of high kVp and low kVp operation repeats. Thus, target high kVp 202 is applied during a high kVp duration 232 from point 218, during risetime 212 and during steady-state high kVp 220, to point 224. Low kVp is applied during a low kVp duration 234 from point 224, during falltime 214 and during steady-state low kVp 226, to point 230, and the process repeats.

In order to obtain imaging information, high and low kVp imaging data is integrated during the periods of high and low kVp operation. In embodiments of the invention, high and low kVp triggering for integration occurs during respective rise and falltimes. Thus, as an example, still referring to FIG. 6, high kVp integration 236 begins at point 238, which occurs during a portion of risetime 212, during all of steady-state high kVp 220 operation, and during a portion of falltime 214, to point 240, when low kVp integration begins. Correspondingly, low kVp integration 242 begins at point 240, which occurs during a portion of falltime 214, during all of steady-state low kVp 226 operation, and during a portion of the subsequent risetime that begins at point 230 to point 244. In embodiments of the invention there is no delay or deadtime between high kVp and low kVp integration.

In embodiments of the invention, trigger points 238, 240 are selected based on a threshold voltage or on a selected time during respective rise and falltimes 212, 214. However, it is to be understood that integration for both high and low kVp acquisitions may be caused to occur during steady-state operation of high kVp, low kVp, or both. In one embodiment, no part of steady-state high kVp occurs during low kVp integration because, if steady state high kVp is integrated into a low kVp spectrum, material decomposition performance may be degraded.

Actual or effective high and low kVps measured are dependent upon not only respective high and low target kVps 202, 204, but also on trigger points 238, 240 for high and low integration. Because integration for high and low kVp occurs during respective rise and falltimes, total signal integration is likewise affected by the selected points 238, 240 for high and low integration. As an illustration, referring to FIG. 6, high kVp integration 236 occurs during a period of not only steady-state high kVp operation 220, but during a portion of risetime 212 from point 238 to point 222, and during a portion of falltime 214 from point 224 to 240. As such, an integrated average or effective high kVp 246 results that is somewhat lower than target high kVp 202, because high kVp integration 236 occurs during portions of both risetime 212 and falltime 214 that are each lower in voltage than target high kVp 202. Likewise, an integrated average or effective low kVp 248 results that is somewhat greater than target low kVp 204, because low kVp integration 242 occurs during portions of falltime 214 and the subsequent risetime beginning at point 230 that are each greater in voltage than target low kVp 204. As such, an effective energy difference 250 results between high kVp shots 208 and low kVp shots 210, and effective energy difference 250 is dependent, for at least the reasons discussed, on the operating parameters of high and low kVp operation. As understood in the art, integration of rise and/or falltime may complicate integrated low and high kVp spectrums, which should be accounted for in a CT calibration procedure, during data correction, and during material decomposition processing.

Thus, referring back to FIG. 5, step 106 includes establishing high and low kVp viewtimes, which in an example are at respective locations 232 and 234 of FIG. 6. Given the gantry rotation speed, as selected at step 104, and a desired angular sampling (in the example above, ~1000 view pairs of high and low kVp for each rotation), view times for high and low kVp are selected that optimize acquired high and low kVp sinograms. And, for the example of ~1000 view pairs for each rotation, it is to be understood that the ~1000 views each include a high kVp shot and a low kVp shot. As such, for this example, approximately 2000 integrations are performed for each rotation. Further, despite commanding a constant current setting for a filament, according to one embodiment, filament current is allowed to float during kVp switching. As such, the optimization disclosed herein accounts for and tolerates responses in filament current such that overall system performance and data acquisition is optimized.

In addition, mA realized is also a function of kVp. Thus, according to one embodiment, commanded mA is constant, but despite this mA realized floats and therefore changes with applied kVp. Consequently, an approximate ⅓ drop in realized mA is typically experienced at low kVp compared to high kVp, despite a constant mA setting. Further, the low kVp generates generally lower energy x-rays, that are less penetrating. Accordingly, more mAs or mA times integration time is typically needed to achieve a desired signal. In one embodiment, the mA for the low kVp is maximized and therefore a longer integration time is required to achieve the desired mAs. Thus, low kVp duration 234 is illustrated as significantly greater in duration than high kVp duration 232.

Further, it is to be recognized that kVp rise and falltimes are generally lower for high mA. Thus, in one embodiment a relatively high mA is selected for high kVp operation and, due to mA dependence on kVp and tube filament temperature, mA for low kVp operation is approximately ⅔ of mA for high kVp operation. As such, it is to be understood that viewtimes may be first selected based on the above parameters and conditions, and such initial settings may be based on the application (inferring patient motion), and a subject to be imaged. Information regarding the subject to be imaged may be obtained a priori from a scout scan, from accumulated tables of imaging information, or from information obtained from the subject in a prior scan, as examples. Likewise, high and low kVp integration times and trigger points are established at step 108 of FIG. 5, and may be based on anticipated signal levels or noise levels as understood in the art. Resulting effective high and low kVps are determined at step 110, which may be obtained in a manner consistent with timing diagram 200 of FIG. 6. The effective high and low kVps are influenced, as discussed, by risetimes and falltimes, by the portions of the rise and falltimes that are integrated into the view, and the target high and low steady-state kVps.

As such, and as illustrated in FIG. 6, imaging parameters are selected in order to optimize a signal-to-noise ratio for a dual kVp imaging acquisition. As is understood in the art, because an amount of attenuation through a body or object is a function of kVp, signal-to-noise ratio (SNR) for an acquisition at a first kVp may not be the same as SNR for an acquisition at a second kVp. As such, overall SNR may not be optimized for fast kVp switching based on parameters selected in steps 102-108. And, in order to obtain adequate SNR for such applications, unnecessary and excess dose may be applied to a patient in order to obtain adequate SNR. Thus, process 100 includes a number of iteration steps for optimizing SNR for high kVp ($SNR_H$) and SNR for low kVp ($SNR_L$) to avoid excess dose while realizing an adequate SNR for high and low kVp views.

An optimization function in material decomposition relates $SNR_H$ and $SNR_L$ to image quality of material density, and relates $SNR_H$ and $SNR_L$ to monochromatic representations, effective atomic number, and other image representations derived from high and low kVp acquisitions. In one embodiment a goal is to balance $SNR_H$ and $SNR_L$ such that they are approximately equal to one another. However, one skilled in the art will recognize that there are other optimization functions for optimizing $SNR_H$ and $SNR_L$. Thus, referring back to FIG. 5, after effective high and low kVps are obtained at step 110, an inquiry is made at step 112 as to whether $SNR_H$ and $SNR_L$ are optimized. If $SNR_H$ and $SNR_L$ are not optimized 114, then one or a combination of system parameters are adjusted at step 116, wherein the system parameters adjusted include, but are not limited to, gantry speed, high and low kVp view times, high and low kVp integration times, and high and low kVp trigger points. After adjustment of system parameters at step 116, effective high and low kVps are again obtained at step 110, and a determination is again made at step 112 as to whether $SNR_H$ and $SNR_L$ are optimized. The iteration continues through steps 110-116 until $SNR_H$ and $SNR_L$ are optimized at step 112, and, once optimized, high and low kVp imaging data is acquired having optimized $SNR_H$ and $SNR_L$ at step 118.

As one example, in an iteration having a selected high and low kVp (step 102) and a selected gantry speed (step 104), wherein the iteration does not include changing gantry speed, because the gantry speed is unchanged, and because the number of views is unchanged, total integration time for high kVp integration 236 and low kVp integration 242 is unchanged. As such, in order to affect $SNR_H$ with respect to $SNR_L$, trigger points for integration and/or integration times themselves may be iterated upon, however such is to be done with the constraint that total integration time is unchanged. Thus, high kVp integration 236 time may be increased and low kVp integration 242 may correspondingly be decreased, however their sum, in this example, remains unchanged. Accordingly, effective high and low kVps determined at step 110 may be altered, thus affecting $SNR_H$ with respect to $SNR_L$ in this example.

A controller, such as controller 28 of FIG. 2, is configured to generate an image using integrated data, according to an embodiment of the invention. In one embodiment the controller is configured to generate the image using integrated data from multiple steady-state periods acquired during portions of the gantry rotation, each steady-state period containing one of the first kVp for the first time period and the second kVp for the second time period. In another embodiment, the controller is configured to calculate $SNR_H$ with $SNR_L$ and to adjust the operating parameter for all steady-state periods before a CT acquisition begins. In another embodiment, the controller is configured to adjust the operating parameter for multiple steady-state periods based in part on integration data in a previous steady-state period.

Referring now to FIG. 10, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4 or 5. A conveyor system 520 also is provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

An implementation of the system 10 and/or 510 in an example comprises a plurality of components such as one or more of electronic components, hardware components, and/or computer software components. A number of such components can be combined or divided in an implementation of the system 10 and/or 510. An exemplary component of an implementation of the system 10 and/or 510 employs and/or comprises a set and/or series of computer instructions written in or implemented with any of a number of programming languages, as will be appreciated by those skilled in the art. An implementation of the system 10 and/or 510 in an example comprises any (e.g., horizontal, oblique, or vertical) orientation, with the description and figures herein illustrating an exemplary orientation of an implementation of the system 10 and/or 510, for explanatory purposes.

An implementation of the system 10 and/or the system 510 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 510 comprises the recordable data storage medium of the image reconstructor 34, and/or the mass storage device 38 of the computer 36. A computer-readable signal-bearing medium for an implementation of the system 10 and/or the system 510 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 510, for instance, one or more of a telephone network, a local area network ("LAN"), a wide area network ("WAN"), the Internet, and/or a wireless network According to an embodiment of the invention, a CT system includes a rotatable gantry having an opening for receiving an object to be scanned, an x-ray source coupled to the gantry and configured to project x-rays through the opening, a generator configured to energize the x-ray source to a first kVp and to a second kVp that is lower than the first kVp, a detector attached to the gantry and positioned to receive x-rays from the x-ray source that pass through the opening, and a controller configured to energize the x-ray source to the first kVp for a first time period subsequently energize the x-ray source to the second kVp for a second time period different from the first, integrate data from the detector for a first integration period that includes a portion of a steady-state period of the x-ray source at the first kVp, integrate data from the detector for a second integration period that includes a portion of a steady-state period of the x-ray source at the second kVp, compare a signal-to-noise ratio (SNR) during the first integration period ($SNR_H$) and the second integration period ($SNR_L$), adjust an operating parameter of the CT system to optimize an $SNR_H$ with $SNR_L$, and generate an image using the integrated data.

According to another embodiment of the invention, a method of acquiring energy sensitive CT imaging data using a CT imaging system includes applying a first voltage potential to an x-ray source for a first time duration, applying a second voltage potential to the x-ray source for a second time duration that is greater than the first time duration, acquiring imaging data during a first integration period that includes when the x-ray source emits x-rays at a steady-state at the first potential, acquiring imaging data during a second integration period that includes when the x-ray source emits x-rays at a steady-state at the second potential, optimizing a first signal-to-noise ratio (SNR) during the first integration period with a second SNR during the second integration period by adjusting at least one operating parameter of the CT imaging system, and generating a dual-energy CT image using imaging data acquired after adjusting the at least one operating parameter of the CT imaging system.

According to yet another embodiment of the invention, a computer readable storage medium having stored thereon a computer program comprising instructions which when executed by a computer cause the computer to apply a first kVp potential to an x-ray source to obtain a first kVp steady-state operation of a CT imaging system, apply a second kVp potential to the x-ray source to obtain a second kVp steady-state operation of the CT imaging system, integrate a first set of imaging data that includes data obtained from x-rays generated during a time period when the x-ray source is at the first kVp steady-state operation, integrate a second set of imaging data that includes data obtained from x-rays generated during a time period when the x-ray source is at the second kVp stead-state operation, compare a first signal-to-noise ratio (SNR) of the integrated first set of imaging data with a second SNR of the integrated second set of imaging data, and adjust at least one operating parameter of the CT imaging system based on the comparison.

According to still another embodiment of the invention, a method of establishing first and second integration periods for acquisition of fast-switching dual-energy CT data in a CT system includes determining a first signal-to-noise ratio (SNR) for the first integration period, determining a second SNR for the second integration period, comparing the first SNR to the second SNR, and adjusting an operating condition of the CT system based on the compared first SNR and the second SNR.

A technical contribution for the disclosed method and apparatus is that it provides for a computer-implemented apparatus and method of acquiring imaging data at more than one energy range using a multi-energy imaging source.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:
1. A CT system comprising:
a rotatable gantry having an opening for receiving an object to be scanned;
an x-ray source coupled to the gantry and configured to project x-rays through the opening;

a generator configured to energize the x-ray source to a first kVp and to a second kVp that is lower than the first kVp;

a detector attached to the gantry and positioned to receive x-rays from the x-ray source that pass through the opening; and a controller configured to:
  energize the x-ray source to the first kVp for a first time period;
  subsequently energize the x-ray source to the second kVp for a second time period different from the first;
  integrate data from the detector for a first integration period that includes a portion of a steady-state period of the x-ray source at the first kVp;
  integrate data from the detector for a second integration period that includes a portion of a steady-state period of the x-ray source at the second kVp;
  compare a signal-to-noise ratio (SNR) during the first integration period ($SNR_H$) and the second integration period ($SNR_L$);
  adjust an operating parameter of the CT system to optimize an $SNR_H$ with $SNR_L$; and
  generate an image using the integrated data.

2. The CT system of claim 1 wherein the controller is configured to generate the image using integrated data from multiple steady-state periods acquired during portions of the gantry rotation, each steady-state period containing one of the first kVp for the first time period and the second kVp for the second time period.

3. The CT system of claim 1 wherein the controller is configured to calculate $SNR_H$ with $SNR_L$ and to adjust the operating parameter for all steady-state periods before a CT acquisition begins.

4. The CT system of claim 1 wherein the controller is configured to adjust the operating parameter for multiple steady-state periods based in part on integration data in a previous steady-state period.

5. The CT system of claim 1 wherein the operating parameter comprises one of a gantry speed, a kVp viewtime, a view integration time, and an integration trigger point.

6. The CT system of claim 1 wherein the data for the first integration period and the data for the second integration period are integrated having no deadtime therebetween.

7. The CT system of claim 1 wherein the controller is configured to command a constant filament current setting.

8. The CT system of claim 7 wherein the controller is configured to command a constant mA setting during the first time period and the second time period.

9. The CT system of claim 1 wherein the controller is configured to cause integration of one of the first and second integration periods to begin or end during one of a risetime from low kVp to high kVp and a falltime from high kVp to low kVp.

10. The CT system of claim 1 wherein the controller is configured to acquire a scout scan of the object prior to energizing the x-ray source to the first time period.

11. The CT system of claim 1 wherein a sum of the first integration period and the second integration period is less than 1 ms.

12. The CT system of claim 1 wherein the controller is configured to adjust the operating parameter such that $SNR_H$ is approximately equal to $SNR_L$.

13. A method of acquiring energy sensitive CT imaging data using a CT imaging system, comprising:

applying a first voltage potential to an x-ray source for a first time duration;

applying a second voltage potential to the x-ray source for a second time duration that is greater than the first time duration;

acquiring imaging data during a first integration period that includes when the x-ray source emits x-rays at a steady-state at the first potential;

acquiring imaging data during a second integration period that includes when the x-ray source emits x-rays at a steady-state at the second potential;

optimizing a first signal-to-noise ratio (SNR) during the first integration period with a second SNR during the second integration period by adjusting at least one operating parameter of the CT imaging system; and generating a dual-energy CT image using imaging data acquired after adjusting the at least one operating parameter of the CT imaging system.

14. The method of claim 13 wherein the step of optimizing comprises adjusting one of a gantry speed, a kVp viewtime, a view integration time, and an integration trigger point.

15. The method of claim 13 wherein acquiring imaging data during the second imaging period includes acquiring the imaging data during the second imaging period immediately after the first integration period such that there is no deadtime therebetween.

16. The method of claim 13 comprising commanding a constant filament current to be applied to a filament while applying both the first voltage potential and the second voltage potential.

17. The method of claim 13 comprising commanding a constant mA to be applied between a cathode and an anode while applying both the first voltage potential and the second voltage potential.

18. The method of claim 13 comprising acquiring a scout scan prior to applying the first voltage potential and the second voltage potential.

19. The method of claim 13 wherein the step of optimizing comprises adjusting the at least one operating parameter such that the first SNR is approximately equal to the second SNR.

20. A non-transitory computer readable storage medium having stored thereon a computer program comprising instructions which when executed by a computer cause the computer to:

apply a first kVp potential to an x-ray source to obtain a first kVp steady-state operation of a CT imaging system;

apply a second kVp potential to the x-ray source to obtain a second kVp steady-state operation of the CT imaging system;

integrate a first set of imaging data that includes data obtained from x-rays generated during a time period when the x-ray source is at the first kVp steady-state operation;

integrate a second set of imaging data that includes data obtained from x-rays generated during a time period when the x-ray source is at the second kVp stead-state operation;

compare a first signal-to-noise ratio (SNR) of the integrated first set of imaging data with a second SNR of the integrated second set of imaging data; and adjust at least one operating parameter of the CT imaging system based on the comparison.

21. The computer readable storage medium of claim 20 wherein the operating parameter comprises one of a gantry speed, a kVp viewtime, a view integration time, and an integration trigger point.

22. The computer readable storage medium of claim 20 wherein the computer is caused to integrate at least one of the first and second sets of imaging data during a risetime from one of the first and second kVps to the other of the first and second kVps.

23. The computer readable storage medium of claim 22 wherein the computer is caused to integrate at a time that begins during the risetime.

24. The computer readable storage medium of claim 20 wherein the computer is caused to acquire a scout scan prior to applying the first kVp potential and the second kVp potential.

25. The computer readable storage medium of claim 20 wherein the computer is caused to adjust the at least one operating parameter such that the first SNR is approximately equal to the second SNR.

* * * * *

UNITED STATES PATENT AND TRADEMARK OFFICE
CERTIFICATE OF CORRECTION

PATENT NO. : 7,826,587 B1　　　　　　　　　　　　　　　　　　　　　　　　Page 1 of 1
APPLICATION NO. : 12/558248
DATED : November 2, 2010
INVENTOR(S) : Langan et al.

It is certified that error appears in the above-identified patent and that said Letters Patent is hereby corrected as shown below:

In Column 4, Line 7, delete "stead-state" and insert -- steady-state --, therefor.

In Column 12, Line 23, delete "stead-state" and insert -- steady-state --, therefor.

In Column 14, Line 57, in Claim 20, delete "stead-state" and insert -- steady-state --, therefor.

Signed and Sealed this
Twenty-eighth Day of December, 2010

David J. Kappos
*Director of the United States Patent and Trademark Office*